United States Patent [19]

Greene et al.

[11] Patent Number: 4,582,051
[45] Date of Patent: Apr. 15, 1986

[54] CERVICAL COLLAR WITH CIRCUMFERENTIAL AND VERTICAL HEIGHT ADJUSTABILITY AND STABILITY

[75] Inventors: Ted J. Greene, La Canada; George P. Irons, West Covina, both of Calif.

[73] Assignee: United States Manufacturing Company, Pasadena, Calif.

[21] Appl. No.: 578,125

[22] Filed: Feb. 8, 1984

[51] Int. Cl.⁴ .......................... A61F 5/08; A61F 5/04
[52] U.S. Cl. ................... 128/76 R; 128/87 B; 128/DIG. 23; 128/DIG. 19
[58] Field of Search .............. 128/76 R, 68, 69, 87 B, 128/DIG. 19, DIG. 23

[56] References Cited

U.S. PATENT DOCUMENTS 2,735,424  2/1956  Benjamin ............... 128/DIG. 23
2,820,455  1/1958  Hall ......................... 128/87 B
4,515,153  5/1985  Calabrese ............ 128/DIG. 23 X

*Primary Examiner*—Richard J. Apley
*Assistant Examiner*—Kathleen D'Arrigo
*Attorney, Agent, or Firm*—Christie, Parker & Hale

[57] ABSTRACT

A cervical collar has a mandibular plate for supporting a patient's chin, an occipital plate for supporting the occipital region of the patient's head, flexible front and rear neck supports extending around the opposite sides of the patient's neck from the mandibular support plate and the occipital support plate, and releasable fastening means on the front and rear supports for providing circumferential support around the patient's neck. A sternal plate rests on the patient's sternum, a scapular plate on the scapular region of the patient's back, and lower front and rear flexible shoulder supports extend over the right and left shoulders of the patient. Releasable fastening means adjust the circumferential size of the shoulder supports. An elongated rigid front support bar extends from the mandibular plate to the sternal plate. Cooperating fasteners on the front support bar and on the sternal plate releasably adjust the height of the mandibular plate independently of the the sternal plate. An elongated rigid rear support bar extends from the occipital plate to the scapular plate. Cooperating fasteners on the rear support bar and on the scapular plate releasably adjust the height of the occipital plate independently of the scapular plate. The fastening means for the mandibular support and the occipital support resist downward pressures and any twisting forces normally encountered during use of the cervical collar to provide a stable means of immobilizing the patient's head and upper cervical spine region during use.

4 Claims, 8 Drawing Figures

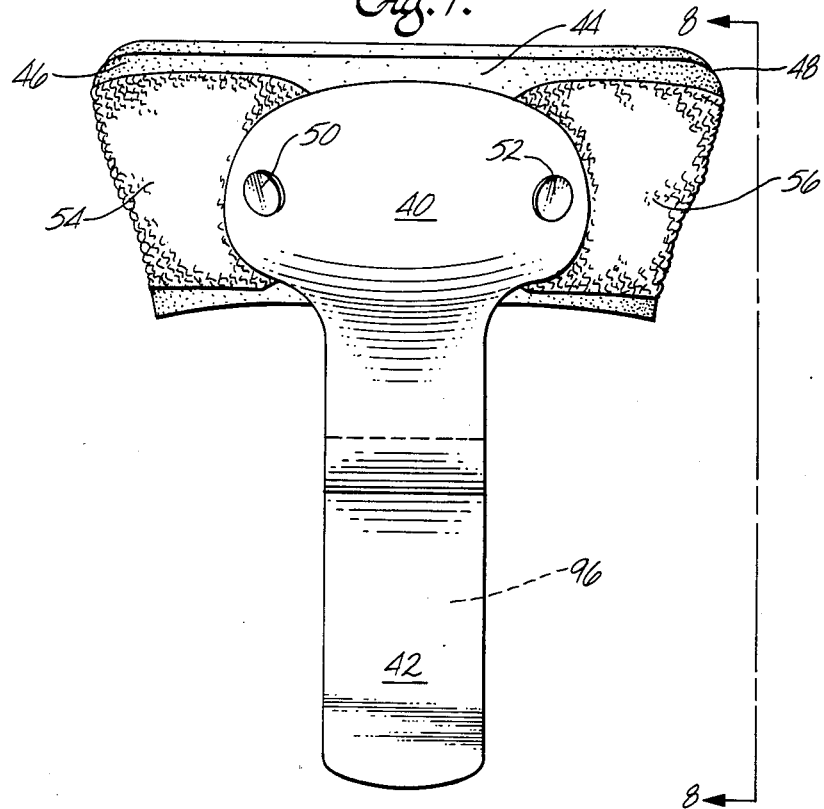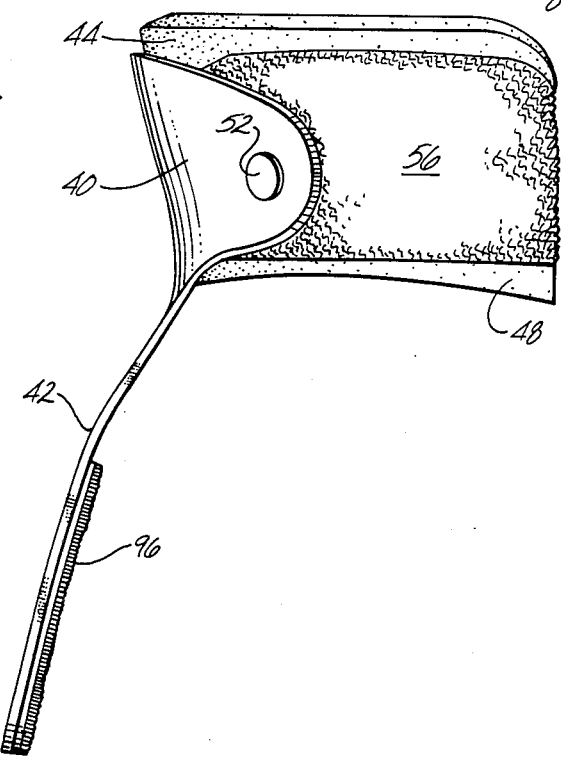

CERVICAL COLLAR WITH CIRCUMFERENTIAL AND VERTICAL HEIGHT ADJUSTABILITY AND STABILITY

FIELD OF THE INVENTION

This invention relates to an improved cervical collar, and more particularly to a light weight cervical collar having circumferential and vertical height adjustability with extreme stability in all adjusted positions.

BACKGROUND OF THE INVENTION

In the past, there have been different types of cervical collars used on patients who have suffered neck injuries. The cervical collar provides rigid support for the cervical vertebrae to immobilize the vertebrae while relieving pressures on the cervical nerves by supporting the head and preventing undue pressures from being applied to the neck. A cervical collar should maintain front to back stability of the patient's head in addition to preventing rotation of the head. It is also desirable to maintain stability in other angular positions of the head such as by holding the head in flexion, or extension, or by holding the head in extreme capital flexion.

Since a cervical collar may be worn by a patient over a long period of time, it is also important for the cervical collar to be comfortable. The cervical collar should be adjustable to adapt to various neck sizes while maintaining the required rigid support in different adjustable positions. An adjustable cervical collar is more useful if it can be applied quickly and easily while adjusting to various neck sizes, rather that being a custom-made or custom-adjusted device.

A popular cervical collar, known as the Philadelphia collar, is disclosed in U.S. Pat. No. 3,756,226 to Calabrese et al. The Philadelphia collar is formed in two halves and each half is made from a closed cell polymeric material. Each half is adjustably coupled to the other half and one half supports the chin while the other half extends along the spine from the back to the basal portion of the skull. The Philadelphia collar currently requires twelve different sizes, four sizes for different heights and three circumferential sizes.

The present invention provides a one size adjustable cervical collar that can be adjusted to match all of the circumferential and vertical height adjustments of the Philadelphia collar. Moreover, the cervical collar of this invention adapts to different angles for maintaining the head in extension, flexion, or extreme capital flexion, or other angular orientations of the head, while also maintaining extreme stability of the collar in these various angular positions. The collar is infinitely adjustable to these various angular positions and is extremely stable in its resistance to up and down angular movement, side to side angular movement, or rotation of the head. The cervical collar also is extremely light in weight and comfortable when worn, as well as quickly and easily applied and adjusted to fit the particular neck size of the patient and to adjust to the desired angular position in which the head is immobilized.

SUMMARY OF THE INVENTION

Briefly, one embodiment of this invention provides an adjustable cervical collar having a mandibular plate for supporting a patient's chin, an occipital plate for supporting the occipital region of the patient's head, and upper front and rear circumferential support means on the mandibular plate and the occipital plate for extending around the neck and to releasable attachment for each other to hold the mandibular plate and the occipital plate at a desired distance from one another when supporting the mandible and the occipital region of the patient's head. A sternal plate rests on the patient's sternum and a scapular plate rests on the scapular region of the patient's back. Lower front and rear circumferential support means on the sternal plate and the scapular extend around the shoulder regions of the patient for releasable attachment to each other to hold the sternal plate and the scapular plate in a desired fixed position relative to each other when supported on the sternal and scapular regions of the patient. An elongated rigid front support bar extends down from the mandibular plate to the sternal plate. Cooperating front fastening means on the front support bar and on the sternal plate releasably secure the front support bar at infinitely adjustable positions in vertical height along the sternal plate to adjust the vertical height of the mandibular plate independently of the position of the sternal plate. An elongated rigid rear support bar extends down from the occipital plate to the scapular plate. Cooperating rear fastening means on the rear support bar and on the scapular plate releasably secure the rear support bar at infinitely adjustable positions in vertical height along the scapular plate to adjust the vertical height of the occipital plate independently of the position of the scapular plate. The front fastening means are releasably attachable with a sufficient force of resistence to separation that resists downward pressure on the mandibular plate normally encountered during use while also resisting side pressures normally encountered during use sufficient to resist twisting of the front support bar relative to the sternal plate. The rear fastening means are releasably attachable with a sufficient force of resistence to separation to resist downward pressures on the occipital plate normally encountered during use while also resisting side pressures normally encountered during use sufficiently to resist twisting of the rear support bar relative to the scapular plate.

The cervical collar is thus infinitely adjustable in vertical height at the front and at the rear so that the patient's head can be held in essentially any desired angular position, while the collar, once adjusted, provides good resistance to up or down rotation of the head, tipping of the head from side to side, or twisting of the head. The cervical collar also is circumferentially adjustable around the patient's neck and around the patient's shoulder region to adjust to these various sizes. This adjustability in combination with the independent vertical adjustability in the front and rear makes the collar especially suitable for easy and quick adjustments to any of the desired positions of the patient's head.

These and other aspects of the invention will be more fully understood by referring to the following detailed description and the accompanying drawings.

DRAWINGS

FIG. 7 is a front elevation view of the occipital plate of the cervical collar.

FIG. 8 is a side elevation view taken on line 8—8 of FIG. 7.

DETAILED DESCRIPTION

Figure 1:
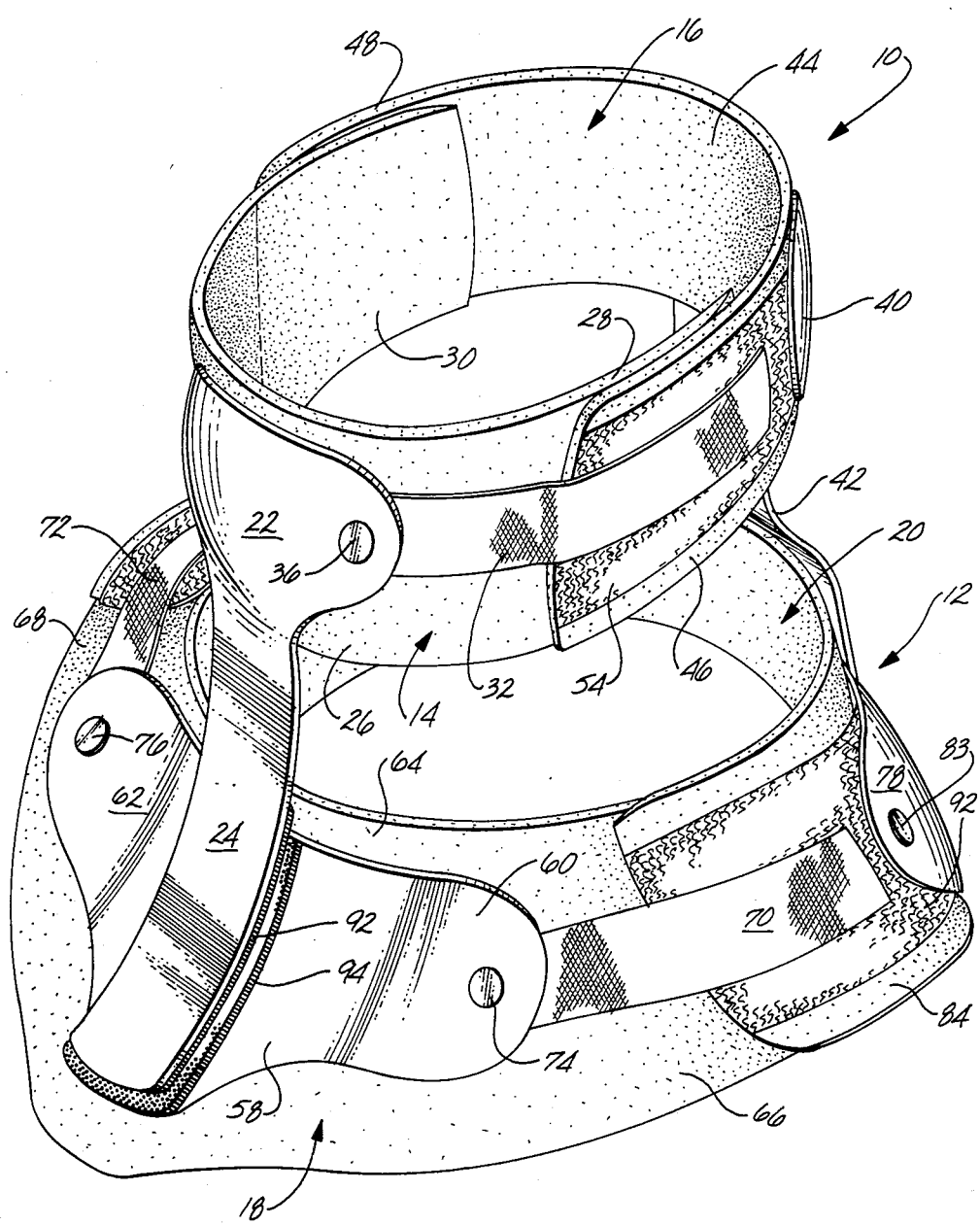
FIG. 1 is a front perspective view showing a completely assembled cervical collar according to principles of this invention.
Figure 2:
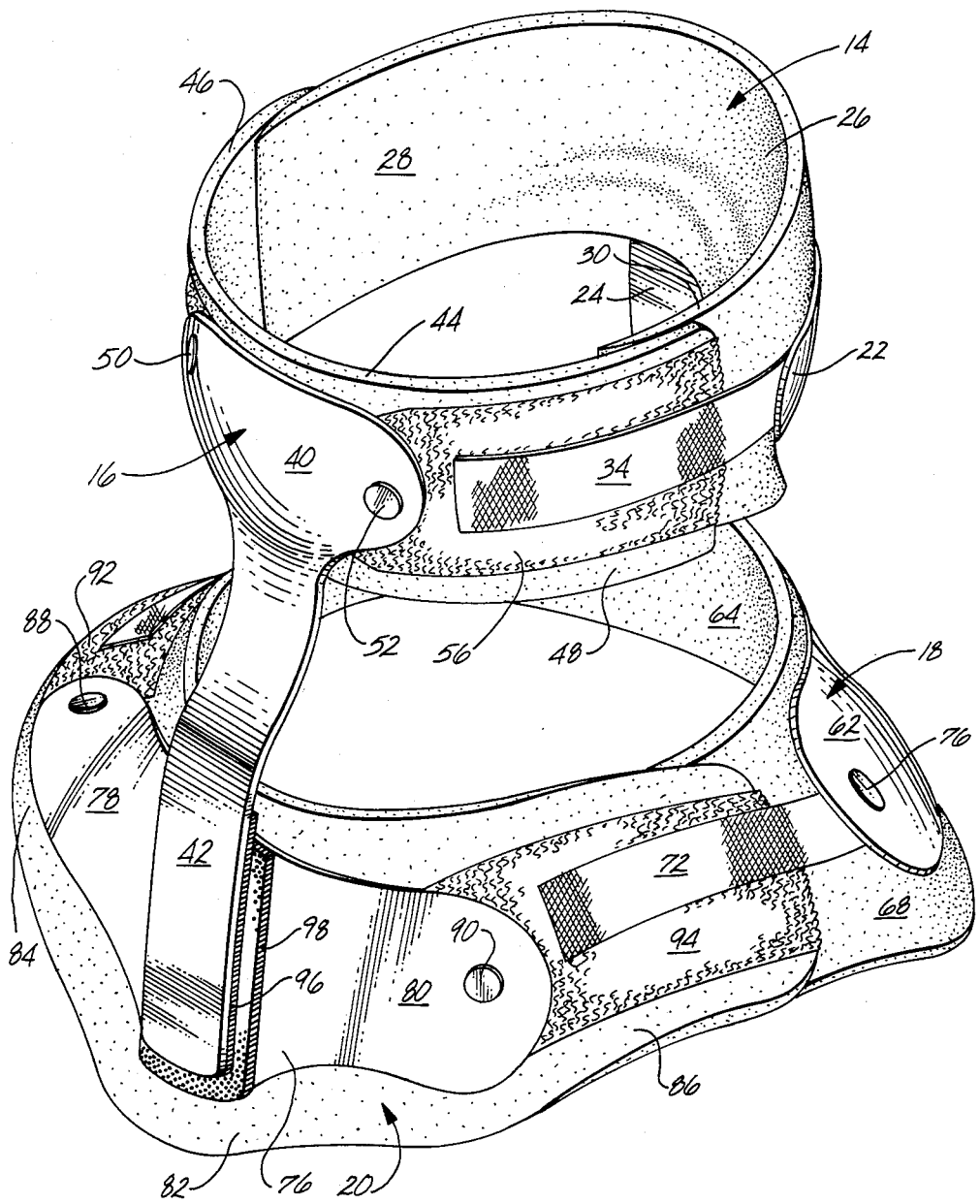
FIG. 2 is a rear perspective view of the cervical collar shown in FIG. 1.

FIGS. 1 and 2 are front and rear perspective views, respectively, showing a completely assembled cervical collar according to principles of this invention. The cervical collar includes an upper circumferential support 10 for extending around the neck region of the patient, and a lower circumferential support 12 for extending around the shoulder region of the patient. The two circumferential supports are spaced vertically from one another and this vertical spacing is adjustable. The front vertical spacing is adjustable independently of the vertical spacing in the rear. The circumferential size of each circumferential support also is adjustable. Other adjustments also are possible as will become better understood by the description of follow.

The upper circumferential support 10 includes a front half 14 for supporting the lower jaw or mandibular region of the patient and a rear half 16 for supporting the rear or occipital region of the patient's head. The lower circumferential support 12 includes a front half 18 for resting on the sternal or upper chest region of the patient, and a rear half 20 for resting on the scapular or upper central portion of the patient's back immediately below the neck.

Figure 5:
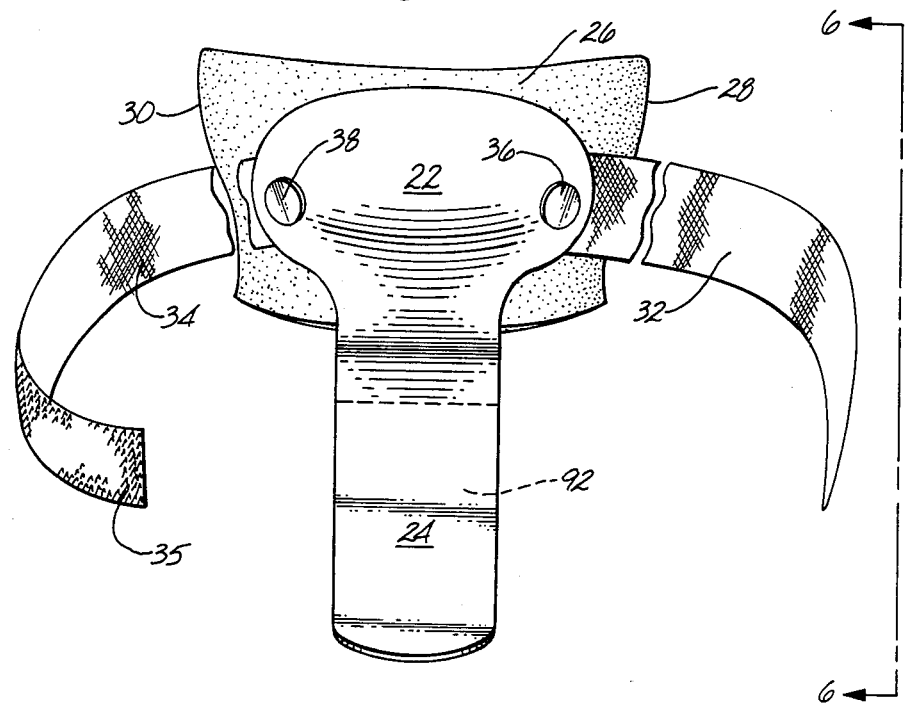
FIG. 5 is a front elevation view of the mandibular plate of the cervical collar.
Figure 6:
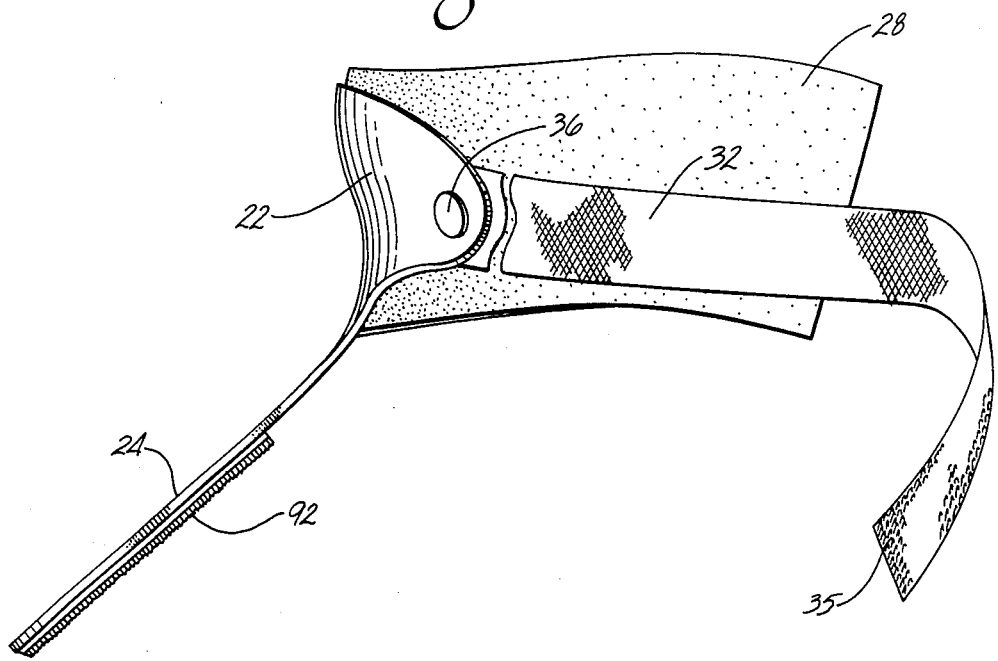
FIG. 6 is a side elevation view taken on line 6—6 of FIG. 5.

The front half 14 of the upper circumferential support is understood best by referring to FIGS. 1, 5 and 6. This means of support includes a thin, rigid light weight plastic bar having an enlarged cup shaped upper portion 22 for forming a mandibular support plate. The upper portion narrows at its bottom to form an elongated downwardly extending front leg 24. The downward extent of the front leg is outwardly at an angle below and to the front of the upper portion 22 of the bar. A U-shaped front neck support 26 is rigidly affixed to the inside face of the mandibular support plate 22. The front neck support preferably comprises a soft, flexible, resilient polymeric plastic piece having left and right flexible free end portions 28 and 30 extending away from the left and right sides of the mandibular support plate. In this application the terms "right" and "left" are with reference to the collar as assembled and worn. The front portion of the front neck support 26 is adapted to provide a soft means of support for the front and underside of the patient's lower jaw while the flexible free ends 28 and 30 provide a flexible means of support to wrap around the opposite sides of the neck. Flexible left and right straps 32 and 34 also are affixed to the mandibular plate and extend away from the opposite left and right sides of the mandibular plate. These straps overlie the flexible free ends 28 and 30 of the U-shaped front neck support attached to the mandibular plate. The inside faces of the flexible straps 32 and 34 have thistle cloth fastener material such as a hook fastener 35 sold under the trademark Velcro. Left and right fasteners 36 and 38 rigidly affix the left and right straps 32 and 34 to opposite sides of the mandibular plate 22. These fasteners also fasten the U-shaped front neck support 26 to the mandibular plate, although the flexible U-shaped piece also can be affixed to the mandibular plate by adhesive bonding.

The rear half 16 of the upper circumferential support is understood best by referring to FIGS. 2, 7, and 8. This rear means of support includes a thin, lightweight rigid plastic bar having an enlarged cup shaped upper portion 40 for providing an occipital support plate. The enlarged upper portion 40 narrows at its bottom to form an elongated downwardly extending rear leg 42. The downward extent of the rear leg is outward at an angle below and to the rear of the upper portion 40 of the support. A flexible U-shaped rear neck support 44 is rigidly affixed to the inside face of the occipital support plate 40. The U-shaped rear neck support preferably comprises a soft, flexible, resilient plastic piece having flexible left and right free ends 46 and 48 extending away from left and right sides of the occipital support plate 40. Left and right fasteners 50 and 52 rigidly affix the flexible rear neck support 44 to the inside face of the occipital support plate 40, although the support 44 also can be adhesively bonded to the occipital support plate. Left and right sections 54 and 56 of a Velcro pile fastener are secured to the outer faces of the flexible free ends of the flexible U-shaped rear neck support.

In the preferred embodiment, the front support bar that provides the mandibular support 22 and the front support leg 24 as well as the rear support bar that provides the occipital support 40 and the rear support leg 42 are both made of a light weight but hard plastic material such as Kydex. This material is a stiff material that maintains the rigidity of the front and rear mandibular and occipital supports and their respective support legs during use of the cervical collar. The shape of each lower support leg can be adjusted by heating and then bending them to the desired anatomical shape. The U-shaped flexible front and rear neck support pieces 26 and 44 are preferably made from a closed cell polymeric plastic material such as polyethylene or polyurethene. Plastazote is the preferred material.

Figure 3:
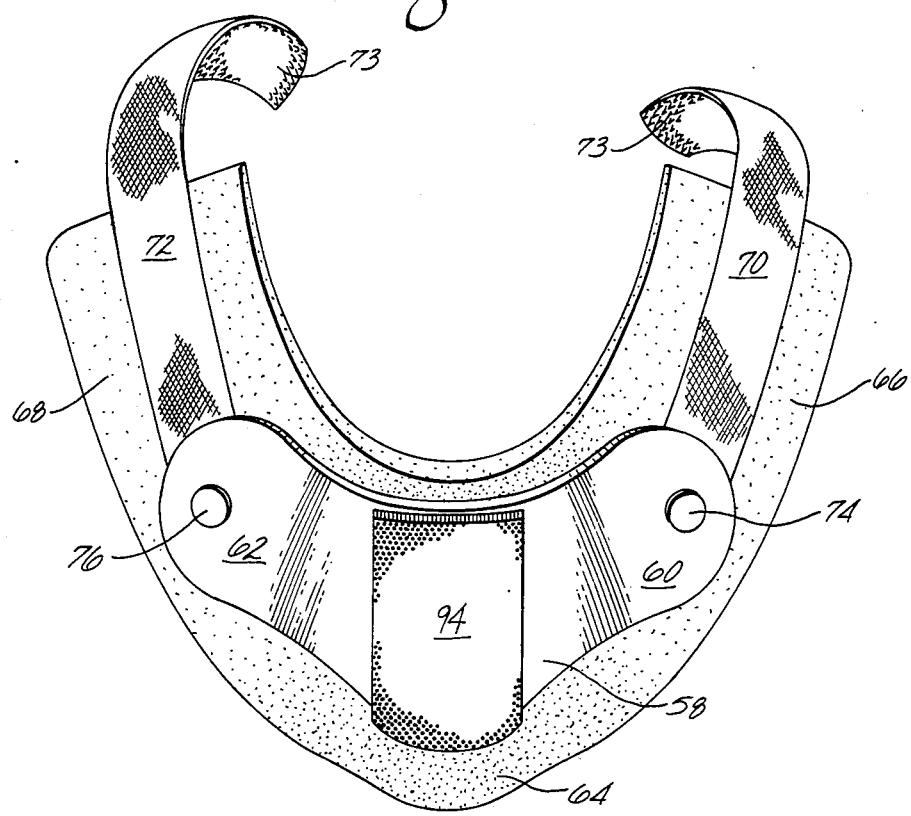
FIG. 3 is a top view of the sternal plate of the cervical collar.

The front half 18 of the lower circumferential support 12 includes a thin rigid plastic piece for forming a sternal support plate 58. This support plate is shaped to the anatomical configuration of the front of the chest region, and it has an enlarged central region with narrowed left and right extensions 60 and 62, respectively, extending outwardly over the left and right portions of the upper sternum. The sternal support plate is shown best in FIGS. 1 and 3. A generally U-shaped soft, thin, flexible, resilient front shoulder support 64 is affixed to the inside face of the sternal support plate 58. This support has flexible left and right free ends 66 and 68 for extending over the front left and right shoulder regions of the patient. Flexible left and right straps 70 and 72 are affixed to the left and right undersides of the sternal support plate. The flexible straps overlie the left and right free ends 66 and 68 of the flexible front shoulder support 64. The inside faces of the lower front straps have a Velcro hook fastener 73. Left and right fasteners 74 and 76 rigidly affix the left and right straps 70 and 72 to the left and right portions 60 and 62 of the sternal support plate 58. These fasteners also rigidly affix the U-shaped flexible front shoulder support 64 to the sternal support plate 58, although it can also be affixed by adhesive bonding.

Figure 4:
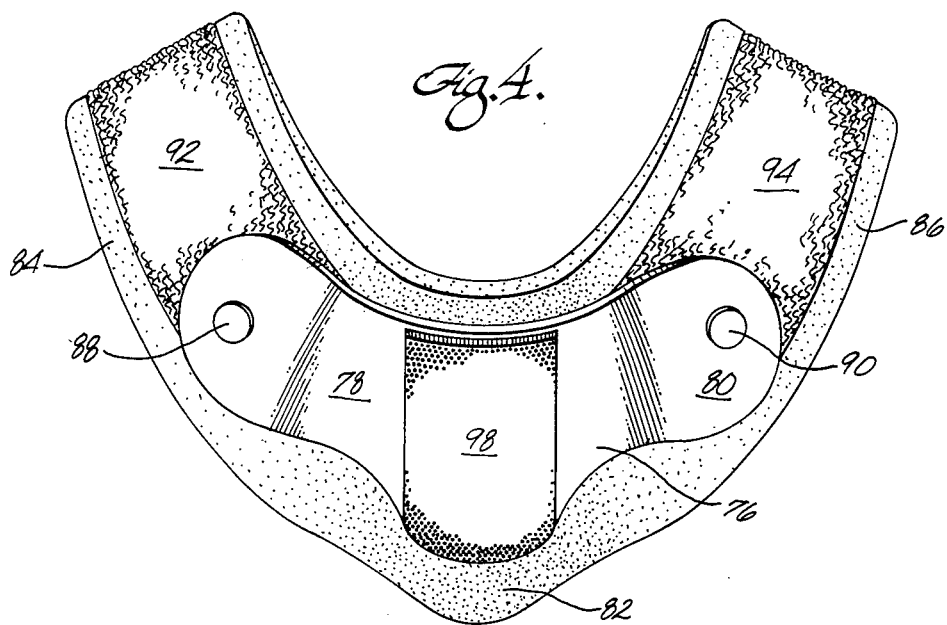
FIG. 4 is a top view of the scapular plate of the cervical collar.

The rear half 20 of the lower circumferential support 12 includes a thin, rigid plastic piece for forming a scapular support plate 76. This support plate is shaped to the anatomical configuration of the upper central portion of the back region and has an enlarged central region which narrows to left and right extensions 78 and 80, respectively, for extending outwardly over the left and right portions of the upper sternum. The scapular support is best shown in FIGS. 2, and 4. A generally U-shaped soft, thin, flexible resilient rear support 82 is affixed to the inside face of the scapular support plate 76. This flexible support has an enlarged central region which narrows to flexible left and right free ends 84 and 86 for extending over the rear left and right shoulder regions of the patient. Left and right elongated sections 92 and 94 of a Velcro hook material overlie the outer faces of the flexible left and right free ends 84 and 86 of the flexible rear shoulder support plate 76. Left and right fasteners 88 and 90 on the left and right sides of the scapular support rigidly affix the flexible rear shoulder support to the inside face of the scapular support plate, although the flexible support also can be secured to the scapular plate by adhesive bonding.

The sternal support plate 58 and the scapular support plate 76 are both made from a hard but light weight plastic material such as Kydex which can be heated for bending into the desired anatomical shape. The flexible front and rear shoulder supports attached to the inside faces of the sternal and scapular support plates are both preferably made from a soft, flexible, closed cell polymeric plastic material such as polyethylene or polyurethane. Plastazote is the preferred material. The flexible plastic pieces on both the mandibular support and the occipital support as well as the sternal support and scapular support are preferably heat formed or drape formed over a mold. The opposite free ends of these flexible plastic pieces are preferably tapered narrower such as by skyving. It is also preferable that the soft flexible plastic pieces all cover a wider anatomical area than their associated rigid support plates.

An elongated front fastener section 92 is affixed to the inside face of the leg 24 that extends down from the mandibular support plate 22. A cooperating elongated front fastener section 94 is on the central front face of the sternal support plate 58. At the rear of the cervical collar an elongated rear fastener section 96 is on the inside face of the leg 42 that extends down from occipital support plate 40. A cooperating elongated rear fastener section 98 is on the central front face of the scapular support plate 76. It is of critical importance that these cooperating fastener sections be capable of infinite positional adjustments, one relative to the other, both lengthwise and rotationally. It is also of critical importance that they can be pressed together into releasable contact and released by being pulled apart. It is also important that the fasteners have sufficient resistance to separation that they have a good level of resistance to axial sliding movement one relative to the other, while also having a good level of resistance to side pressures that would otherwise tend to twist one section relative to the other. A preferred fastener material is a black dual-lock pressure-sensitive tape sold by 3M Company under product No. 3541.

In using the cervical collar, the sternal support and the scapular support are first placed over the front of the patient's upper chest region and over the scapular region of the patient. The free ends of the flexible front and rear shoulder supports carried on the sternal and scapular supports are then extended over the left and right shoulder regions of the patient and overlapped as shown in FIGS. 1 and 2. The flexible straps 70 and 72 on the scapular support are fixed to the Velcro fastener sections 92 and 94 after the desired circumferential size of the lower circumferential support is adjusted to the sternal, scapular and shoulder size of the patient. With the lower circumferential support in place the sternal plate 58 and scapular plate 76 provide a rigid means of support for the mandibular and occipital support bars of the upper circumferential support. The upper circumferential support is then placed around the patient by placing the mandibular support plate 22 under the patient's chin and the occipital support plate 40 under the occipital region of the patient's head, while the patient's head is held in the desired position. The front leg 24 below the mandibular support plate and the rear leg 42 below the occipital support then can be extended downwardly to the sternal and scapular support plates, and the cooperating fastener sections 92, 94, and 96, 98 can be pressed into contact. The flexible free ends of the front and rear neck supports attached to the mandibular and occipital are wrapped around opposite sides of the patient's neck region. The flexible straps 32 and 34 on the mandibular support are affixed to the Velcro fasteners 54 and 56 to hold the upper circumferential support in firm contact around the patient's neck. The free ends of the flexible neck supports on the mandibular and occipital support plates can be overlapped as shown in FIGS. 1 and 2; and the adjacent Velcro fasteners can then be pressed into contact to adjust to the neck size of the patient and to retain the circumferential pressure provided by the mandibular support, the occipital support, and the surrounding circumferential support provided by the flexible front and rear neck supports. The dual-lock pressure-sensitive fasteners provide infinite adjustments in the vertical height of the mandibular support above the sternal support, while independently providing infinite adjustments in the vertical height of the occipital support above the scapular support. This allows infinite adjustments in the angle at which the patient's head is held such as in flexion or extension. Moreover, the mandibular support bar and the occipital support bar can be bent to various shapes so the patient's head can be held in extreme capital flexion, for example. The dual lock fasteners also permit slight tipping of the head to the left or the left and immobilizing at that angular position if desired. The fasteners cooperate with their rigid support members to be releasably attached with a sufficient force of resistance to separation that will resist downward pressures on the mandibular plate normally encountered during use while also resisting side pressures normally encountered during use sufficient to resist twisting of the front support bar relative to the sternal plate. The rear fasteners are releasably attachable also with a sufficient force of resistance to separation to resist downward pressures on the occipital plate normally encountered during use while also resisting side pressures normally encountered during use sufficiently to resist twisting of the rear support bar relative to the scapular plate.

Thus, the cervical collar can be fitted to patients with adjustments in the size of the patient's neck, adjustments for the size of the patient's shoulder region, adjustments for vertical height both at the front and rear, while holding these adjustments to safely immobilize the patient's head and cervical region in the desired position. The cervical collar can be easily applied and all adjustments made quickly and easily. Moreover, the cervical collar is light in weight and therefore comfortable during prolonged use.

What is claimed is:

1. An adjustable cervial collar comprising:

(A) an upper circumferential support means for extending around and supporting the neck region of a patient comprising (1) an upper front half for supporting the lower jaw of the patient, and (2) a separate upper rear half for supporting the occipital region of the patient's head;

the upper front half including (a) a generally U-shaped front neck-supporting piece preformed from a soft, flexible, resilient closed cell plastic foam material for extending adjacent opposite sides of the patient's neck region; and (b) a thin, flat, rigid chin support member having an enlarged cup-shaped mandibular support overlying and affixed to a front central portion of the flexible U-shaped front neck-supporting piece for supporting the underside of the patient's chin and leaving flexible free end portions of the U-shaped front neck-supporting piece for extending along opposite sides of the patient's neck region, and an elongated front support leg extending from the mandibular support downwardly past and spaced a substantial distance below a bottom edge of the front neck-supporting piece;

the upper rear half including (c) a generally U-shaped rear neck-supporting piece preformed from a soft, flexible, resilient closed cell plastic foam material for extending adjacent opposite sides of the patient's neck region; and (d) a thin, flat, rigid occipital support member having an enlarged cup-shaped occipital support overlying and affixed to a rear central portion of the U-shaped rear neck-supporting piece for supporting the occipital region of the patient's head and leaving flexible free end portions of the flexible U-shaped rear neck-supporting piece for extending along opposite sides of the patient's neck region, and an elongated rear support leg extending from the occipital support downwardly past and spaced a substantial distance below a bottom edge of the U-shaped rear neck-supporting piece;

the flexible free end portions of the U-shaped front and rear neck-supporting pieces overlapping each other along opposite sides of the patient's neck region to provide an adjustable continuous upper circumferential support of said soft, flexible, resilient closed-cell foam material held in a fixed position around the patient's neck as the rigid chin support and occipital support are in contact with the patient's chin and occipital region, respectively; and further including adjustable upper fastening means on the upper front and rear halves for releasably securing the flexible free end portions of the U-shaped front and rear neck-supporting pieces to each other in infinitely adjustable overlapping and fixed relative positions to provide said adjustable continuous upper circumferential support held in a fixed position around the patient's neck; and (B) a lower circumferential support means for extending around the shoulder region of the patient comprising (3) a lower front half for support on the chest region of the patient, and (4) a separate lower rear half for support on the back of the patient, the lower front half including (e) a generally U-shaped front sternal support piece preformed from a soft, flexible, resilient closed cell plastic foam material for resting on the sternal region of the patient and extending therefrom over opposite front sides of the shoulder regions of the patient; and (f) a thin, flat, rigid sternal support member shaped to the anatomical configuration of the front of the chest and extending laterally outwardly over left and right portions of the upper sternum, the sternal support member overlying and being affixed to a front central portion of the flexible U-shaped front sternal support piece for support on the upper sternum of the patient and leaving flexible free end portions of the U-shaped front sternal support piece for extending over opposite front sides of the patient's shoulder region;

the lower rear half including (g) a generally U-shaped rear scapular support piece preformed from a soft, flexible, resilient closed cell plastic foam material for resting on the scapular region of the patient and extending therefrom over opposite rear sides of the shoulder regions of the patient; and (h) a thin, flat, rigid scapular support member shaped to the anatomical configuration of the upper central portion of the patient's back region and extending laterally outwardly over left and right portions of the patient's upper back region, the scapular support member overlying and being affixed to a rear central portion of the flexible U-shaped rear scapular support piece for support on the scapular region of the patient's back and leaving flexible free end portions of the U-shaped rear scapular support piece for extending over opposite rear sides of the patient's shoulder region;

the flexible free end portions of the U-shaped front and rear sternal and scapular support pieces overlapping each other along opposite sides of the patient's shoulder regions to provide an adjustable continuous lower circumferential support of said soft, flexible, resilient closed cell foam material held in a fixed position around the patient's shoulder regions as the rigid sternal and scapular support members are in contact with the patient's chest and upper back regions, respectively; and further including adjustable lower fastening means on the lower front and rear halves for releasably securing the flexible free end portions of the U-shaped front and rear sternal and scapular support pieces to each other in infinitely adjustable overlapping and fixed positions to provide said adjustable continuous lower circumferential support held in a fixed position around the patient's shoulder regions;

the front support leg of the chin support member extending downward sufficiently to overlap the sternal support member; and including cooperating front fastening means on the front support leg and on the sternal support member for releasably securing the front support leg at infinitely adjustable positions along the sternal support member to adjust the height of the mandibular support independently of the sternal support member for holding the mandibular support in a fixed position supporting the underside of the patient's chin;

the rear support leg of the occipital support member extending downward sufficiently to overlap the scapular support member; and including cooperating rear fastening means on the rear support leg and on the scapular support member for releasably securing the rear support leg at infinitely adjustable positions along the scapular support member to adjust the height of the occipital support independently of the scapular support member for holding the scapular support in a fixed position supporting the occipital region of the patient's head.

2. Apparatus according to claim 1 in which the chin support member, occipital support member, sternal support member and scapular support member are all made from a hard lightweight plastic material.

3. Apparatus according to claim 2 in which the lightweight plastic material can be heat formed for bending each member into a corresponding anatomical shape.

4. An adjustable cervical collar comprising:

(A) an upper circumferential support means for extending around and supporting the neck region of a patient comprising (1) an upper front half for supporting the lower jaw of the patient, and (2) a separate upper rear half for supporting the occipital region of the patient's head;

the upper front half including (a) a generally U-shaped front neck-supporting piece preformed from a soft, flexible, resilient closed cell plastic foam material for extending adjacent opposite sides of the patient's neck region; and (b) a thin, flat, rigid one-piece chin support member made of hard plastic and having an enlarged cup-shaped mandibular support overlying and affixed to a front central portion of the flexible U-shaped front neck-supporting piece for supporting the underside of the patient's chin and leaving flexible free end portions of the U-shaped front neck-supporting piece unsupported by the chin support member for extending along opposite sides of the patient's neck region, and an elongated narrow front support leg extending from the mandibular support downwardly past and spaced a substantial distance below a bottom edge of the front neck-supporting piece;

the upper rear half including (c) a generally U-shaped rear neck-supporting piece preformed from a soft, flexible, resilient closed cell plastic foam material for extending adjacent opposite sides of the patient's neck region; and (d) a thin, flat, rigid one-piece occipital support member made of hard plastic and having an enlarged cup-shaped occipital support overlying and affixed to a rear central portion of the U-shaped rear neck-supporting piece for supporting the occipital region of the patient's head and leaving flexible free end portions of the flexible U-shaped rear neck-supporting piece unsupported by the occipital support member for extending along opposite sides of the patient's neck region, and an elongated narrow rear support leg extending from the occipital support downwardly past and spaced a substantial distance below a bottom edge of the U-shaped rear neck-supporting piece;

the flexible free end portions of the U-shaped front and rear neck-supporting pieces overlapping each other along opposite sides of the patient's neck region to provide an adjustable continuous upper circumferential support of said soft, flexible, resilient closed-cell foam material held in a fixed position around the patient's neck as the rigid chin support and occipital support are in contact with the patient's chin and occipital region, respectively; and further including adjustable upper fastening means on the upper front and rear halves for releasably securing the flexible free end portions of the U-shaped front and rear neck-supporting pieces to each other in infinitely adjustable overlapping and fixed relative positions to provide said adjustable continuous upper circumferential support held in a fixed position around the patient's neck; and (B) a lower circumferential support means for extending around the shoulder region of the patient comprising (3) a lower front half for support on the chest region of the patient, and (4) a separate lower rear half for support on the back of the patient, the lower front half including (e) a generally U-shaped front sternal support piece preformed from a soft, flexible, resilient closed cell plastic foam material for resting on the sternal region of the patient and extending therefrom over opposite front sides of the shoulder regions of the patient; and (f) a thin, flat rigid sternal support member made of hard plastic and having an enlarged central region shaped to the anatomical configuration of the front of the chest and having left and right extensions from the central region for extending laterally outwardly over left and right portions of the upper sternum, the sternal support member overlying and being affixed to a front central portion of the flexible U-shaped front sternal support piece for support unsupported by the sternal support member on the upper sternum of the patient and leaving flexible free end portions of the U-shaped front sternal support piece for extending over opposite front sides of the patient's shoulder region;

the lower rear half including (g) a generally U-shaped rear scapular support piece preformed from a soft, flexible, resilient closed cell plastic foam material for resting on the scapular region of the patient and extending therefrom over opposite rear sides of the shoulder regions of the patient; and (h) a thin, flat rigid scapular support member made of hard plastic and having an enlarged central region shaped to the anatomical configuration of the upper central portion of the patient's back region and having left and right extensions from the central region for extending laterally outwardly over left and right portions of the patient's upper back region, the scapular support member overlying and being affixed to a rear central portion of the flexible U-shaped rear scapular support piece for support on the scapular region of the patient's back and leaving flexible free end portions of the U-shaped rear scapular support piece unsupported by the scapular support member for extending over opposite rear sides of the patient's shoulder region;

the flexible free end portions of the U-shaped front and rear sternal and scapular support pieces overlapping each other along opposite sides of the patient's shoulder regions to provide an adjustable continuous lower circumferential support of said soft, flexible, resilient closed cell foam material held in a fixed position around the patient's shoulder regions as the rigid sternal and scapular support members are in contact with the patient's chest and upper back regions, respectively; and further including adjustable lower fastening means on the lower front and rear halves for releasably securing the flexible free end portions of the U-shaped front and rear sternal and scapular support pieces to each other in infinitely adjustable overlapping and fixed positions to provide said adjustable continuous lower circumferential support held in a fixed position around the patient's shoulder regions;

the front support leg of the chin support member extending downward sufficiently to overlap the sternal support member; and including cooperating front fastening means on the front support leg and on the sternal support member for releasably securing the front support leg at infinitely positions along the sternal support member to adjust the height of the mandibular support independently of the sternal support member for holding the mandibular support in a fixed position supporting the underside of the patient's chin;

the rear support leg of the occipital support member extending dowward sufficiently to overlap the scapular support member; and including cooperating rear fastening means on the rear support leg and on the scapular support member for releasably securing the rear support leg at infinitely adjustable positions along the scapular support member to adjust the height of the occipital support member independently of the scapular support member for holding the scapular support in a fixed position supporting the occipital region of the patient's head.

* * * * *